United States Patent [19]
Neumeyer et al.

[11] Patent Number: 5,700,446
[45] Date of Patent: Dec. 23, 1997

[54] SYNTHESIS OF FERROCENYL PHENYLTROPANE ANALOGS AND THEIR RADIO-TRANSFORMATION TO TECHNETIUM NEUROPROBES FOR MAPPING MONOAMINE REUPTAKE SITES

[75] Inventors: John L. Neumeyer, Wayland; Gilles Tamagnan, Framingham; Yigong Gao, Hopedale, all of Mass.

[73] Assignee: Neuro Imaging Technologies, LLC, Boston, Mass.

[21] Appl. No.: 662,656

[22] Filed: Jun. 13, 1996

[51] Int. Cl.$^6$ .................... A61K 51/00; A61M 36/14
[52] U.S. Cl. .................... 424/1.85; 546/124; 546/125; 424/1.65
[58] Field of Search ................ 424/1.11, 1.37, 424/1.65, 1.85; 546/124, 125, 4, 10, 128, 132; 524/10–16

[56] References Cited

U.S. PATENT DOCUMENTS 5,104,638  4/1992  Nosco ..................... 424/1.1

OTHER PUBLICATIONS

Carroll et al (1995), J. Med. Chem., vol. 38, No. 2, pp. 379–388 "Cocaine and 3β-(4'-Substituted Phenyl)Tropane-2β-Carboxylic Acid Ester and Amide Analogues. New High–Affinity and Selective Compounds for the Dopamine Transporter."

Aronson et al (1996), J. Med. Chem., vol. 39, No. 7, pp. 1560–1563, "Synthesis and Ligand Binding of η$^6$-(2β-Carbomethoxy-3β-Phenyl Tropane) Transition Metal Complexes."

DiZio et al., "Technetium–and Rhenium–Labeled Progestins: Synthesis, Receptor Binding and In Vivo Distribution of an 11β–Substituted Progestin Labeled with Technetium–99 and Rhenium–186," The Journal of Nuclear Medicine 33:558–569 (1992).

Hjelstuen, "Technetium–99m Chelators in Nuclear Medicine," Analyst 120:863–866 (1995).

Jones et al., "Technepine: A Technetium–99m Spect Imaging Agent For Labeling The Dopamine Transporter In Brain," Soc. of Nucl. Med. 37:17P No. 57 (1996).

Kung et al., "Synthesis of New Bis(aminoethanethiol) (BAT) Derivatives: Possible Ligands for $^{99m}$Tc Brain Imaging Agents," J. Med. Chem. 28:1280–1284 (1985).

Kuntschke et al., "New [$^{99m}$Tc]–Cytectrene Amine Compounds as Specific Brain Imaging Agents," J. Label. Comp. Radiopharm. 36:193–203 (1995).

Lewin et al., "2β–Substituted Analogues of Cocaine. Synthesis and Inhibition of Binding to the Cocaine Receptor," J. Med. Chem. 35:135–140 (1992).

Meegalla et al., "Tc–99m Labeled Tropanes As Dopamine Transporter Imaging Agents," Soc. of Nuc. Med. 37:17P No. 56 (1996).

Meegalla et al., "First Example of a $^{99m}$Tc Complex as a Dopamine Transporter Imaging Agent," J. Am. Soc. 117:11037–11038 (1995).

Neumeyer et al., "N–ω–Fluoroalkyl Analogs of (1R)–2β–Carbomethoxy–3β(4–iodophenyl)–tropane (β–CIT): Radiotracers for Positron Emission Tomography and Single Photon Emission Computed Tomography Imaging of Dopamine Transporters," J. Med. Chem. 37:1558–1561 (1994).

Neumeyer et al., "[$^{123}$I]–2β–Carbomethoxy–3β–(4–iodophenyl) tropane: High–Affinity SPECT Radiotracer of Monoamine Reuptake Sites in Brain," J. Med. Chem. 34:3144–3146 (1991).

Pinkerton et al., "Bioinorganic Activity of Technetium Radiopharmaceuticals," J. Chem. Edu. 62:965–973 (1985).

Wenzel et al., "Tc–99m–Markierung von Cymantren–analogen Verbindungen mit verschiedenen Substituenten—Ein neuer Zugang zu Tc–99m Radiodiagnostika," J. Label. Comp. Radiopharm. 31:641–650 (1992).

Wenzel et al., "Tc–99m markierte Östradiol–Derivate Synthese, Organverteilung und Tumor–Affinität," J. Label. Comp. Radiopharm. 34:981–987 (1994).

*Primary Examiner*—John Kight
*Assistant Examiner*—Dameron Jones
*Attorney, Agent, or Firm*—Weingarten, Schurgin, Gagnebin & Hayes LLP

[57] ABSTRACT

Neuroprobes that include rhenium, manganese, and technetium for use in mapping monoamine reuptake sites are disclosed. Non-radioactive tricarbonylrheniumcyclopentadienyl (TRCp) or non-radioactive tricarbonylmanganesecyclopentadienyl (TMCp) phenyltropane analogs are synthesized for use as testing surrogates for radioactive technetium congeners. Ferrocenyl analogs of phenyltropane are disclosed as useful precursors for the preparation of novel tricarbonyltechnetiumcyclopentadienyl (TTCp) phenyltropane analogs in radioactive form.

24 Claims, 5 Drawing Sheets

SYNTHESIS OF FERROCENYL PHENYLTROPANE ANALOGS AND THEIR RADIO-TRANSFORMATION TO TECHNETIUM NEUROPROBES FOR MAPPING MONOAMINE REUPTAKE SITES

GOVERNMENT RIGHTS

Part of the work leading to this invention was made with United States Government support from SBIR Grant No. R44-MH49533 from the National Institutes of Health. Therefore, the U.S. Government has certain rights in this invention.

FIELD OF THE INVENTION

This invention relates to neuroprobes for mapping monoamine reuptake sites in the brain, and more particularly to neuroprobes incorporating rhenium or an isotope of rhenium, manganese or an isotope or manganese, or a radioisotope of technetium for mapping monoamine reuptake sites.

BACKGROUND OF THE INVENTION

A brain consists of a plurality of neurons that interact by exchanging chemical messengers. Each neuron generates neurochemicals, referred to as neurotransmitters, which act at receptor sites on the cellular membrane of a neuron. Receptors are associated with either ion channels through the cellular membrane or with secondary neurochemical messenger systems. By contrast, molecular complexes which transport chemicals across the cellular membrane of a neuron are referred to as reuptake sites. When a neurotransmitter has served its function, it is removed from the vicinity of the receptor by being bound to a reuptake site, which then transports the neurotransmitter to the interior of the neuron.

Just as there are many specialized neurons in the brain, there are also a variety of neurotransmitters, associated receptors, and reuptake sites. The major neurotransmitters, dopamine, norepinephrine, and serotonin, are referred to collectively as the monoamine neurotransmitters.

A neuron can be classified according to the type of neurotransmitter that it uses to communicate with other neurons, with certain types of neurons being found predominantly in particular regions of the brain. For example, the striatal region of a mammalian brain is innervated by neurons using dopamine as a neurotransmitter. The striatum also contains a large number of non-dopaminergic neurons that have dopamine receptors. Certain compounds, such as cocaine and structurally related phenyltropanes, have a preferential affinity for dopamine reuptake sites, and therefore tend to bind to such sites. The effect of a molecule such as cocaine upon a dopamine reuptake site is to inhibit reuptake of the neurotransmitter dopamine, leaving more of the neurotransmitter available in the vicinity of the dopamine receptor.

In certain neurological diseases, distinct groups of neurons lose their normal physiological function. Consequently, the abnormal neurons may behave differently in the presence of some neurotransmitters and may also produce neurotransmitters in a manner that differs from a healthy neuron. For example, Parkinson's disease is caused by the degeneration of some of the dopaminergic neurons, which have a large number of dopamine reuptake sites, in the striatal region of the brain.

The localization of labelled neuroprobes can be used to find specialized neurons within particular regions of the brain. If the binding distribution of the labelled neuroprobe to its reuptake site is abnormal, it may indicate the presence of a neurological disease. Such an abnormal binding distribution can be observed by incorporating a radionuclide within molecules of the neuroprobe with a high binding affinity for the particular reuptake sites of interest. Then, an imaging technique can be used to obtain a representation of the in vivo spatial distribution of the reuptake sites.

Imaging techniques frequently used in diagnostic procedures include single photon emission computed tomography (SPECT) or Positron Emission Tomography (PET). The primary clinical interest in SPECT and PET agents specific for dopamine transporters ($DA_T$) at dopamine reuptake sites is in the diagnosis and staging of Parkinson's disease. It has been demonstrated with [$^{123}$I] (SPECT), [$^{11}$C] (PET), and [$^{18}$F] (PET)-labelled phenyltropanes, a class of ligands which includes cocaine and has high affinity to the dopamine transporter, that the loss of dopamine transporters can be correlated with the severity of Parkinson's disease. However, [$^{123}$I], [$^{11}$C] and [$^{18}$F] are expensive cyclotron-produced radionuclides and are not readily available for clinical applications, such as diagnostic procedures in a hospital.

In other applications of SPECT imaging, the most commonly used radionuclides are heavy metals, such as $^{99m}$technetium. Technetium (Tc) in particular has by far the most desirable nuclear properties for diagnostic imaging. However, heavy metals are very difficult to incorporate into the molecular structure of neuroprobes because such probes are relatively small molecules (molecular weight less than 400). With the advent of commercial generator systems, instant technetium, innovations in chelation, and new chelating agents, there has been renewed interest in the use of $^{99m}$Tc-labelled compounds. At the present time, chemical forms of $^{99m}$Tc are the most widely used radiopharmaceuticals for radionuclide imaging of the brain, liver, lung and skeleton. The chemistry of $^{99m}$Tc has proven difficult, however. This has resulted in the synthesis of few specific $^{99m}$Tc-labelled probes.

The synthesis of a $^{99m}$Tc-labelled tricarbonyltechnetium-cyclopentadiene or "cytectrene" complex bound to various substituents has been described (Kuntschke et al., J. Label. Cmpds. and Radiopharm. 36:193–203 (1995)). Several $^{99m}$Tc chelates have also been attached to biologically active molecules (DiZio et al., J. Nucl. Med. 33:558–569 (1992)). U.S. Pat. No. 5,104,638 to Nosco describes a method of making $^{99m}$Tc-labelled compounds. Estrogens tagged with $^{99m}$Tc-cytechtrene have also been prepared (Wenzel et al., J. Label. Comp. Radiopharm. 34:981–987 (1994)). Other syntheses of Tc-tagged biologically active molecules have been hampered by difficulties in the chemical procedures.

SUMMARY OF THE INVENTION

As the preferred radionuclide for use in a SPECT imaging study is $^{99m}$Tc, the development of $^{99m}$Tc-labelled phenyltropane analogues would provide a useful tool for routine clinical diagnosis of Parkinson's disease. This need is met by the present invention which is directed to tricarbonyltechnetiumcyclopentadienyl (TTCp) phenyltropane analogs and their preparation in radioactive form from novel ferrocenyl precursors. Novel tricarbonylrheniumcyclopentadienyl (TRCp) or tricarbonylmanganesecyclopentadienyl (TMCp) phenyltropane analogs are also featured for use as surrogates for radioactive technetium congeners. Useful TTCp-tagged phenyltropane analogues can be determined by evaluating their TMCp or TRCp surrogates without involving radiochemistry.

In one embodiment, the invention features a neuroprobe for mapping monoamine reuptake sites, the neuroprobe having the formula:

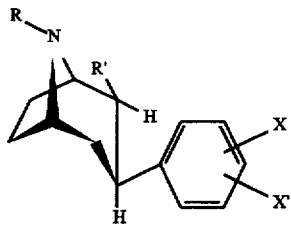

wherein

X=F, Cl, Br, I, H or alkyl; X'=F, Cl, Br, I, H or alkyl; R=alkyl, halogen substituted alkyl, cycloalkyl, halogen substituted cycloalkyl, alkenyl, halogen substituted alkenyl, aryl or halogen substituted aryl; and R'=—(CH$_2$)$_n$Y, wherein Y=—O—C(O)—Z, —C(O)—Z, or —NR"—C(O)—Z; and n=1–6;

and wherein further R"=alkyl, cycloalkyl or H; and Z=

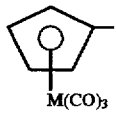

wherein M=rhenium or an isotope of rhenium, manganese or an isotope of manganese, or an isotope of technetium.

In another embodiment, the invention features a neuroprobe for mapping monoamine reuptake sites, the neuroprobe having the formula:

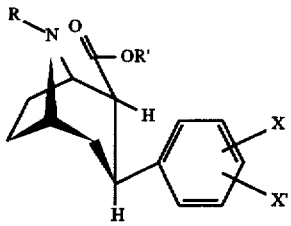

wherein

X=F, Cl, Br, I, H or alkyl; X'=F, Cl, Br, I, H or alkyl; R'=alkyl, halogen substituted alkyl, cycloalkyl, halogen substituted cycloalkyl, alkenyl, halogen substituted alkenyl, aryl or halogen substituted aryl; and R=—(CH$_2$)$_n$Y, wherein Y=—O—C(O)—Z, —C(O)—Z, or —NR"—C(O)—Z; and n=1–6;

and wherein further R"=alkyl, cycloalkyl or H; and Z=

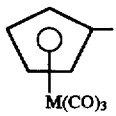

wherein M=rhenium or an isotope of rhenium, manganese or an isotope of manganese, or an isotope of technetium.

In another embodiment, the invention features a neuroprobe for mapping monoamine reuptake sites, the neuroprobe having the formula:

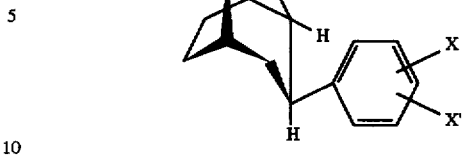

wherein

X=F, Cl, Br, I, H or alkyl; X'=F, Cl, Br, I, H or alkyl; R'=alkyl, halogen substituted alkyl, cycloalkyl, halogen substituted cycloalkyl, alkenyl, halogen substituted alkenyl, aryl or halogen substituted aryl; and R=—(CH$_2$)$_n$Y, wherein Y=—O—C(O)—Z, —C(O)—Z, or —NR"—C(O)—Z; and n=1–6;

and wherein further R"=alkyl, cycloalkyl or H; and Z=

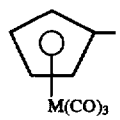

wherein M=rhenium or an isotope of rhenium, manganese or an isotope of manganese, or an isotope of technetium.

The invention also features precursors for the preparation of tricarbonyltechnetiumcyclopentadienyl (TTCp) phenyltropane analogs. In one embodiment, the precursors are of the formula having the core structure:

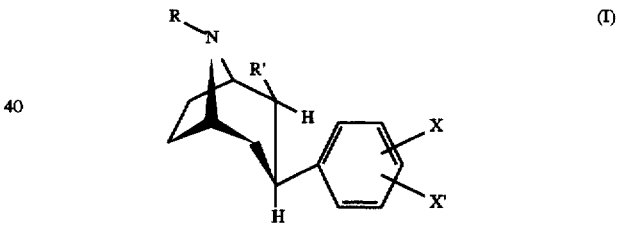 (I)

wherein

X=F, Cl, Br, I, H or alkyl; X'=F, Cl, Br, I, H or alkyl; R=alkyl, halogen substituted alkyl, cycloalkyl, halogen substituted cycloalkyl, alkenyl, halogen substituted alkenyl, aryl or halogen substituted aryl; and R'=—(CH$_2$)$_n$Y, wherein Y=—O—C(O)—Z, —C(O)—Z, or —NR'—C(O)—Z; and n=1–6;

and wherein further R"=alkyl, cycloalkyl or H; and Z=

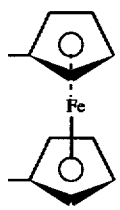

wherein Z is attached to two of the core structure (I), or wherein Z=

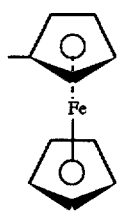

wherein Z is attached to one of the core structure (I).

In another embodiment, the precursors are of the formula having the core structure:

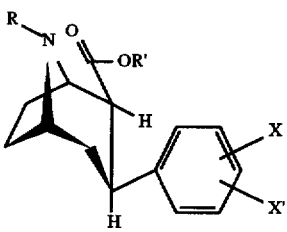
(I)

wherein

X=F, Cl, Br, I, H or alkyl; X'=F, Cl, Br, I, H or alkyl; R'=alkyl, halogen substituted alkyl, cycloalkyl, halogen substituted cycloalkyl, alkenyl, halogen substituted alkenyl, aryl or halogen substituted aryl; and R=—(CH$_2$)$_n$Y, wherein Y=—O—C(O)—Z, —C(O)—Z, or —NR"—C(O)—Z; and n=1–6;

and wherein further R"=alkyl, cycloalkyl or H; and Z=

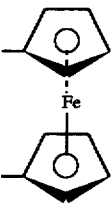

wherein Z is attached to two of the core structure (I), or wherein Z=

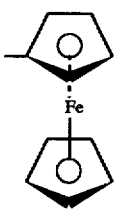

wherein Z is attached to one of the core structure (I).

In another embodiment, the precursors are of the formula having the core structure:

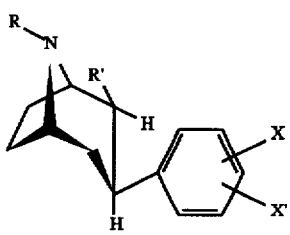
(I)

wherein

X=F, Cl, Br, I, H or alkyl; X'=F, Cl, Br, I, H or alkyl; R'=alkyl, halogen substituted alkyl, cycloalkyl, halogen substituted cycloalkyl, alkenyl, halogen substituted alkenyl, aryl or halogen substituted aryl; and R=—(CH$_2$)$_n$Y, wherein Y=—O—C(O)—Z, —C(O)—Z, or —NR"—C(O)—Z; and n=1–6;

and wherein further R"=alkyl, cycloalkyl or H; and Z=

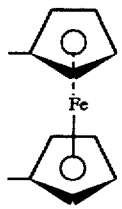

wherein Z is attached to two of the core structure (I), or wherein Z=

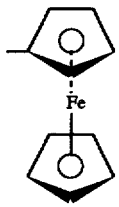

wherein Z is attached to one of the core structure (I).

The ferrocenyl derivatives described above react readily with $^{99m}TcO_4^-$ and a carbonyl donor (M(CO)$_5$Br, M=metal such as Cr or Mn) at 130°–150° C. to transform to radio-labelled [$^{99m}$Tc]-tricarbonyltechnetiumcyclopentadienyl analogs, which are useful for mapping monoamine transporters. Preferably, the X and X' substituents are located in the meta or para positions.

Certain factors must be taken into consideration when radiopharmaceuticals are prepared. An important factor is the time frame during which a radiopharmaceutical must maintain its integrity. When evaluating pharmacokinetics or diagnosing a patient, a medical tracer must remain stable in vivo for the duration of the study to be performed. Analogs incorporating $^{99m}$Tc benefit from a short half-life (approx. 6 hours), which reduces the total radiation dose to the patient. $^{99m}$Tc is also easily detected by a gamma-ray camera due to the emission of a 140 keV photon.

DESCRIPTION OF THE DRAWING

The invention will be more fully understood from the following detailed description taken in conjunction with the accompanying drawings in which.

DETAILED DESCRIPTION OF THE INVENTION

The examples which follow describe methods for preparing tricarbonylrheniumcyclopentadienyl (TRCp) or tricarbonylmanganesecyclopentadienyl (TMCp)-tagged phenyltropane analogs. Methods are also described for preparing novel ferrocenyl precursors or tricarbonyltechnetiumcyclopentadienyl (TTCp)-tagged phenyltropane analogs and their transformation to TTCp compounds labelled with $^{99m}$Tc for use in biological systems.

EXAMPLE I

Preparation of 3β-(4-iodophenyl)-2β-(tricarbonylrheniumcyclopentadienylcarboxymethyl)tropane (RBI-211)

A. Synthesis of 2β-hydroxymethyl-3β-(4-iodophenyl)-tropane-D-Tartrate

Figure 1:
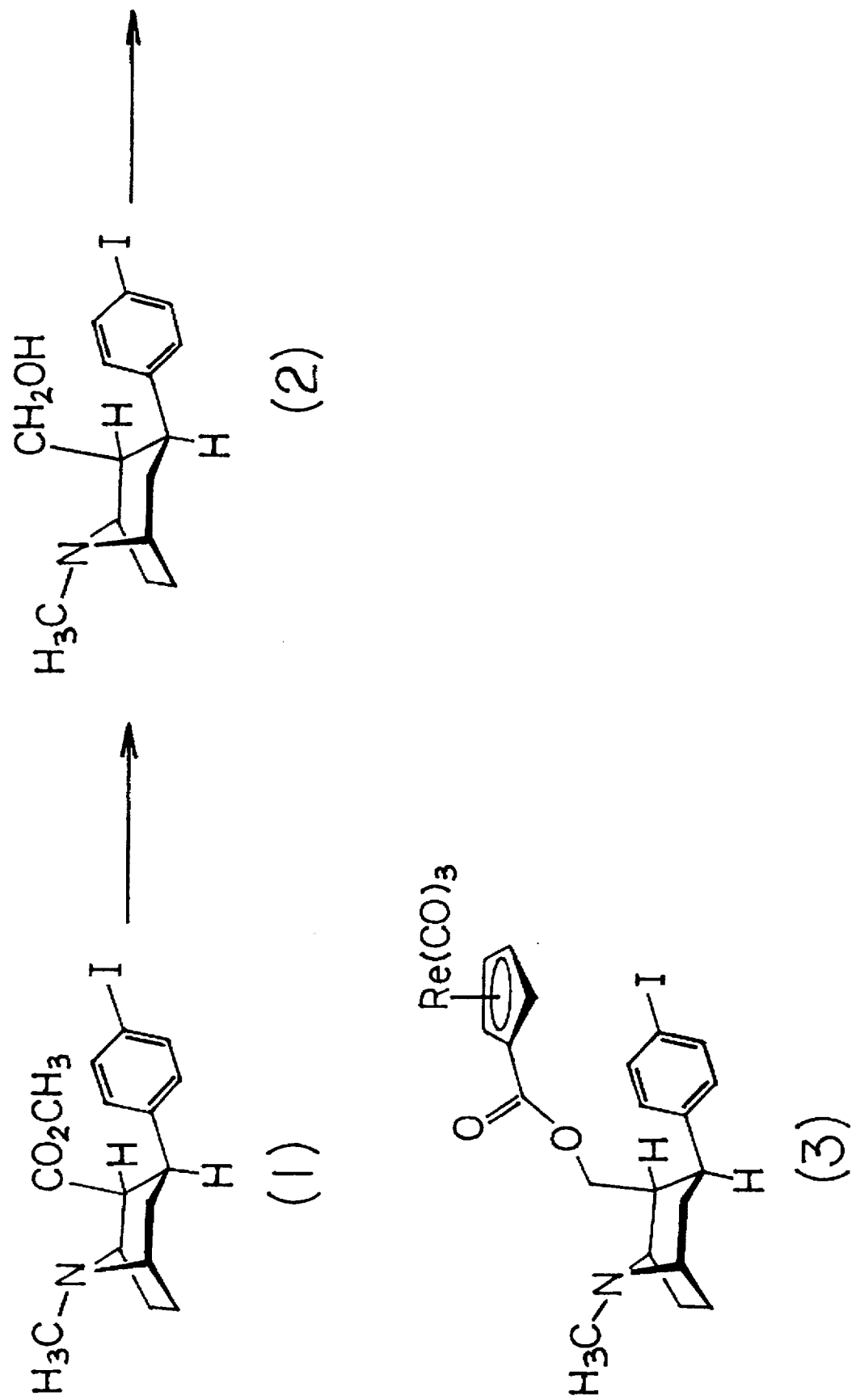
FIG. 1 is a diagram of the synthetic steps in preparing a compound of the invention.

As shown in FIG. 1, 5 mmol 3β-(4-iodophenyl)-2β-(carbomethoxy)tropane (β-CIT (1)) is dissolved in 25 ml ethyl ether at 0° C., and 2 equivalents of lithium borohydride (LiBH$_4$) are added. The temperature is raised to room temperature, and stirring is continued for approximately 2 hr. The reaction is quenched with water and the aqueous phase of the mixture is extracted with methylene chloride. The organic phase is collected and dried over magnesium sulfate and the solvent is removed to give 2β-hydroxymethyl-3β-(4-iodophenyl) tropane free base (2) in quantitative yield. 2β-hydroxymethyl-3β-(4-iodophenyl) tropane was fully characterized as D-tartaric acid: mp=90°–92° C., [α]D$^{20}$ –66.3° C. (c, 0.525, MeOH). $^1$H NMR (250 MHz, CDCl$_3$): δ 7.59 (d, J=8.4 Hz, 2H); 6.99 (d, J=8.4 Hz, 2H); 3.76 (dd, J=11.06 Hz; 1H); 3.44 (d, J=4.59 Hz, 1H); 3.32 (m, 2H); 3.01 (m, 1H); 2.47 (td; J=2.88 Hz, J=12.74 Hz; 1H); 2.20 (s, 3H); 2.16 (m, 2H); 1.70 (m, 2H); 1.65 (m, 1H), 1.46 (m, 1H). Anal. (C$_{15}$H$_{20}$NO$_1$) (C$_4$H$_6$O$_6$): CHN.

B. Synthesis of 3β-(4-iodophenyl)-2β-(tricarbonylrheniumcyclopentadienylcarboxymethyl)tropane, RBI-211 (3)

The produce prepared in step A above (compound 2) is dissolved in toluene (1 g/10 ml) and 1.1 equiv. of triethylamine and 1.1 equiv. of cyclopentadiencarbonyl chloride tricarbonylrhenium are added under nitrogen. After heating at reflux for 30 min., the solvent is removed and the residue is passed through a silica gel column equilibrated with hexane/ether/triethanolamine (50/50/5) to produce 3β-(4-iodophenyl)-2β-(tricarbonylrhenium-cyclopentadienylcarboxymethyl)tropane (3) (RBI-211) in 76% yield. mp: 161°–162° C.; $^1$H NMR (250 MHz, CDCl$_3$). δ 7.59 (d, J=8.4 Hz, 2H); 6.99 (d, J=8.4 Hz, 2H); 5.80 (m, 1H); 5.62 (m, 1H); 5.30 (m, 2H); 4.48 (dd, J=7.57 Hz, J=11.03 Hz; 1H); 53.86 (dd; J=5.86 Hz; J=10.93 Hz, 1H); 3.26 (m, 1H); 3.20 (m, 1H); 3.07 (m, 1H); 2.22 (s; 3H); 2.10 (m, 3H); 1.61 (m, 3H) MS (FAB): 720 (29%): 718 (23%); 340 (100%); Anal. (C$_{24}$H$_{23}$NO$_5$IRe): CHN.

EXAMPLE 2

Preparation of 1,1'-bis-[3β-(4-iodophenyl)tropan-2β-ylmethoxycarbonyl] ferrocene (5)

Figure 2:
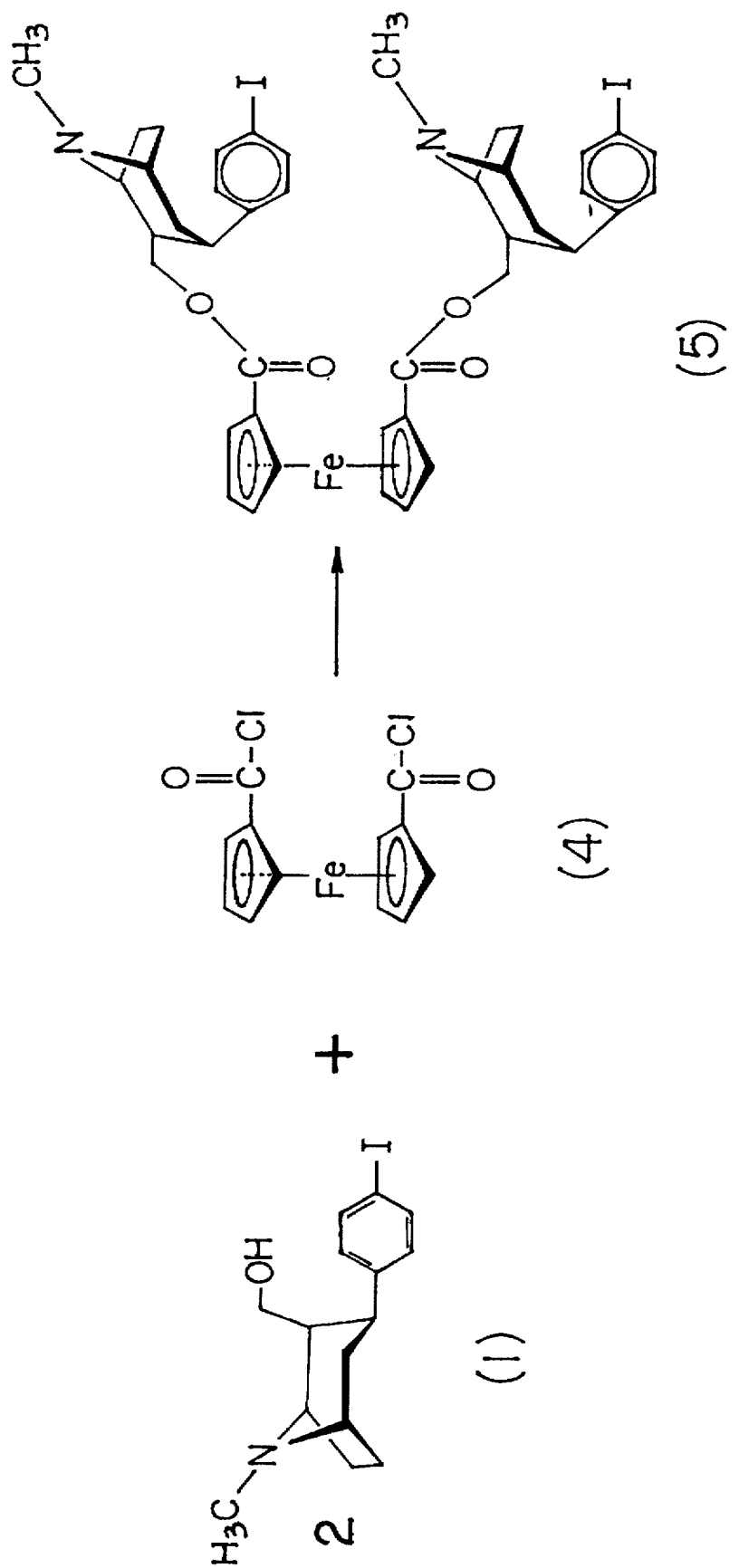
FIG. 2 is another diagram of a series of synthetic steps for preparing another compound of the invention.

As shown in FIG. 2, to a solution of 2β-hydroxymethyl-3β-(4-iodophenyl)tropane (1) in toluene (1 g/10 ml), 1.1 equiv. of triethylamine and 0.5 equiv. of 1,1'-ferrocenedicarbonyl chloride (4) are added under nitrogen. After heating at reflux for 30 min. the solvent is removed, and the residue passed through a silica gel column with hexane/ether/TEA: 50/50/5 to give 1,1'-bis-[3β-(4-iodophenyl)tropane-2β-ylmethoxycarbonyl] ferrocene (5) in 82% yield. mp: 74°–75° C. $^1$H NMR (250 MHz, CDCl$_3$): δ 7.59 (d, J=8.4 Hz, 4H); 6.99 (d, J=8.4 Hz, 4H); 4.57 (s, 4H); 4.36 (m, 6H); 3.85 (m, 2H); 3.30 (m; 4H); 3.06 (m, 2H); 2.29 (s; 6H; 2.17 (m, 8H); 1.68 (m, 2H). Anal. (C$_{42}$H$_{46}$FeNO$_4$I$_2$Re): CHN.

EXAMPLE 3

Preparation of N-(tricarbonylrheniumcyclopentadienylbutan-1-one-4-yl)-2β-carbomethoxy-3β-(4-chlorophenyl)nortropane, RBI-235 (8)

Figure 3:
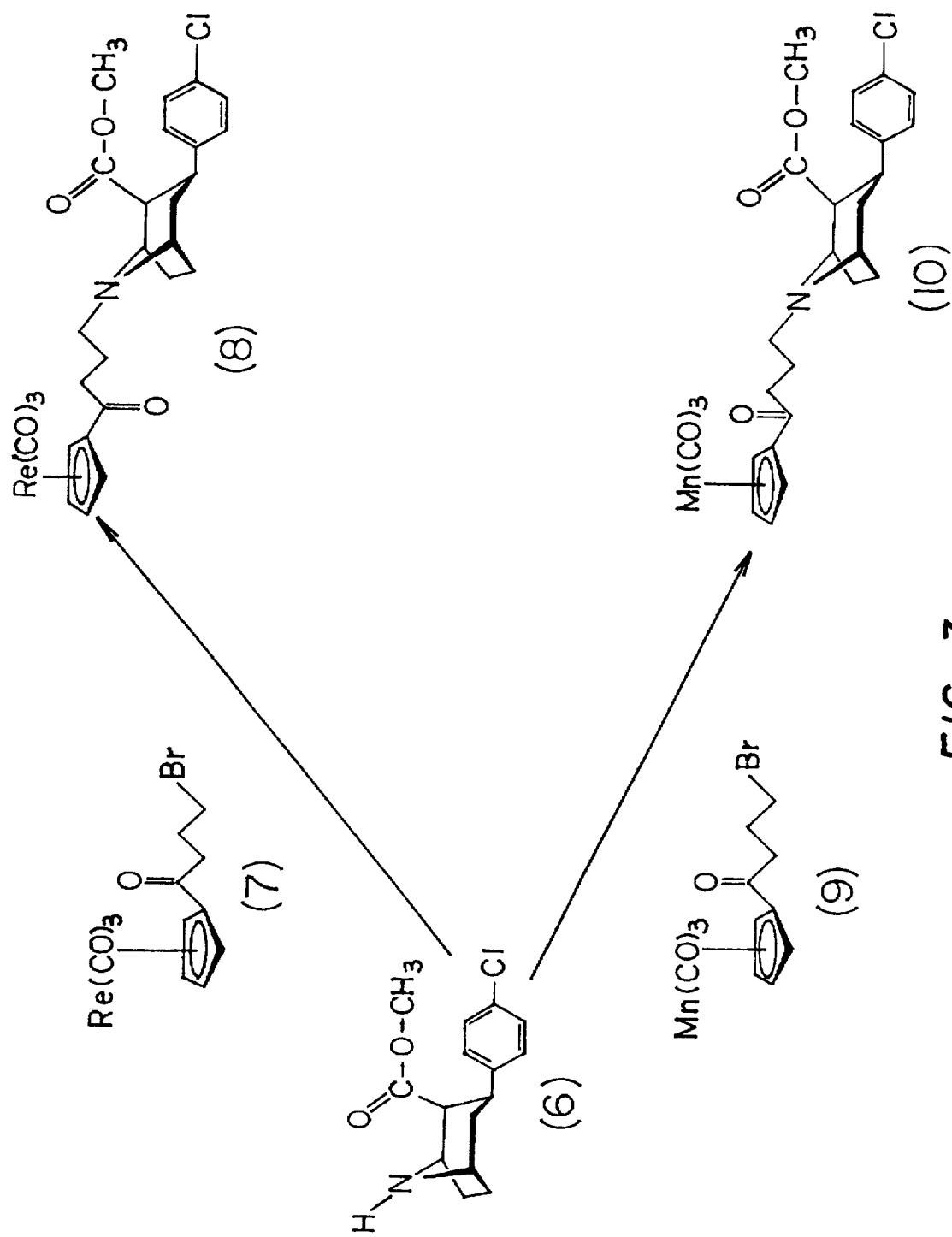
FIG. 3 is another diagram of a series of synthetic steps for preparing compounds of the invention.

As shown in FIG. 3, 4-bromobutan-1-one-cyclopentadiene tricarbonylrhenium (6) (0.4 mmol) and KI (10 mg) are added to a solution of nor-β-CCT (7) (0.27 mmol) and triethylamine (TEA, 46 mmol) in toluene (10 mL). The mixture is refluxed under nitrogen for 3 hours and the progress of the reaction is monitored with thin layer chromatography (TLC). The solvent is removed under reduced pressure and the residue is passed through a silica gel column (equilibrated with a mixture of hexane/ether/triethylamine:50/50/5) to give N-(tricarbonylrheniumcyclopentadienylbutan-1-one-4-yl)-2β-carbomethoxy-3β-(4-chlorophenyl)nortropane (8) (RBI-235) in 64% yield, as a brown oil. Anal. (C$_{27}$H$_{27}$NO$_6$ClRe)$_3$ (H$_2$O): CHN $^1$H NMR: (250 MHz CDCl$_3$): δ 7.19 (dd, J=7.15 Hz, J=7.62 Hz, 4H); 6.11 (s, 1H); 5.05 (s, 1H); 5.39 (m, 2H); 3.69 (m; 1H); 3.49 (m; 5H); 3.36 (m, 1H); 2.89 (m, 3H); 2.62 (m, 1H); 2.29 (m; 2H); 2.05 (m, 1H); 1.71 (m, 3H); 1.21 (m, 2H).

EXAMPLE 4

Preparation of N-(tricarbonylmanganesecyclopentadienylbutan-1-one-4-yl)-2β-carbomethoxy-3β-(4-chlorophenyl)nortropane, RBI-233 (10)

As shown in FIG. 3, N-(tricarbonylmanganesium-cyclopentadienylbutan-1-one-4-yl)-2β-carbomethoxy-3β-(4-chlorophenyl) nortropane (10) is prepared using similar procedures as described in Example 3. 4-Bromobutan-1-one-cyclopentadienetricarbonyl manganese (9) (0.4 mmol) and KI (10 mg) are added to a solution of nor-β-CCT (7) (0.27 mmol) and triethylamine (TEA, 46 mmol) in toluene (10 mL). The mixture is refluxed under nitrogen for 3 hours and the progress of the reaction is monitored with thin layer chromatography (TLC). The solvent is removed under reduced pressure and the residue is passed through a silica gel column (equilibrated with a mixture of hexane/ether/triethylamine:50/50/5) to give N-(tricarbonylmanganesecyclopentadienylbutan-1-one-4-yl)-2β-carbomethoxy-3β-(4-chlorophenyl)nortropane (10) (RBI-233) in 64% yield, as an oil. Anal. (C$_{27}$H$_{27}$NO$_6$ClMn) $_3$(H$_2$O)$_2$:CHN. $^1$H NMR (250 MHz, CDCl$_3$): Δ7.21 (m, 4H); 4.84 (s, 2H); 3.69 (br, 1H); 3.49 (br, 3H); 3.36 (br, 1H); 2.90 (m, 2H); 2.80 (m, 1H); 2.61 (m, 2H); 2.27 (m; 2H); 2.03 (m, 2H); 1.71 (m, 4H); 1.22 (m, 1H).

EXAMPLE 5

Preparation of N-(tricarbonylrheniumcyclopentadienylcarboxypropyl)-2β-carbomethoxy-3β-(4-chlorophenyl)nortropane (RBI-232) (13)

Figure 4:
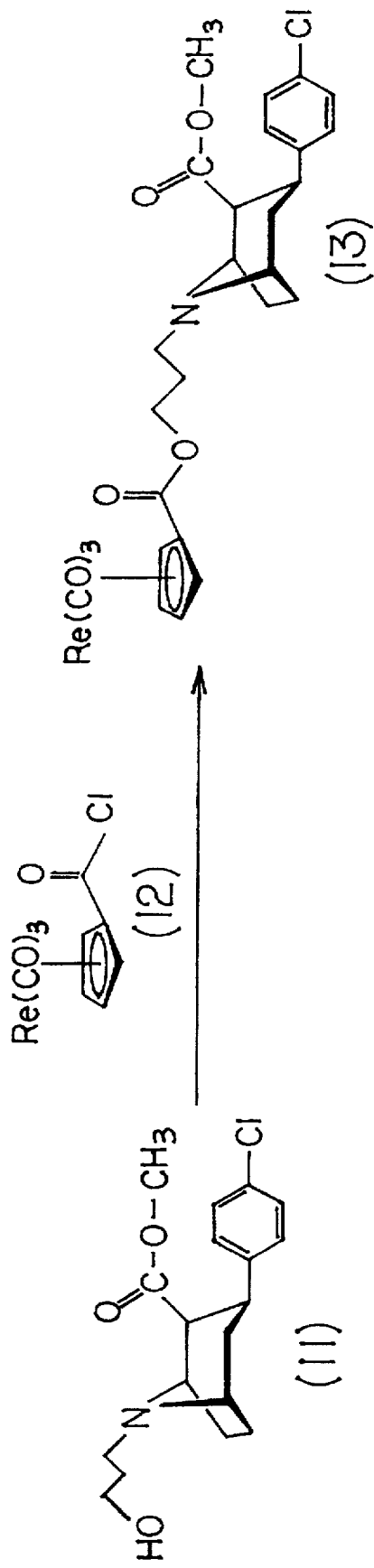
FIG. 4 is another diagram of a series of synthetic steps for preparing another compound of the invention.

As shown in FIG. 4, to a solution of N-(2-hydroxypropyl)-2β-carbomethoxy-3β-(4-chlorophenyl)tropane (11) in toluene (1 g/10 ml) is added 1.1 equiv. of triethylamine (TEA) and 1.1 equiv. of cyclopentadienecarbonyl chloride tricarbonylrhenium (12) under nitrogen. After heating at reflux for 30 min., the solvent is removed and the residue passed through a silica gel column with hexane/ether/TEA:50/50/5 to give N-(tricarbonylrheniumcyclopentadienylcarboxypropyl)-2β-carbomethoxy-3β-(4-chlorophenyl) nortropane (13) (RBI-232) in 45% yield. $^1$H NMR (250 MHz, CDCl$_3$): Δ7.26 (m, 4H); 6.01 (m, 2H); 5.36 (m, 2H); 4.31 (m; 2H); 3.67 (br, 1H); 3.47 (s, 3H); 3.36 (m, 1H); 2.90 (m, 2H); 2.51 (m, 2H); 2.35 (m, 2H); 2.10 (m, 2H); 1.71 (m, 4H). Anal. (C$_{27}$H$_{27}$NO$_7$ClRe) (H$_2$O)$_3$: CHN.

EXAMPLE 6

Preparation of 3β-(4-Chlorophenyl)-2β-tricarbonylrheniumcyclopentadienylcarboxymethyl)tropane, RBI-219 (15)

Figure 5:
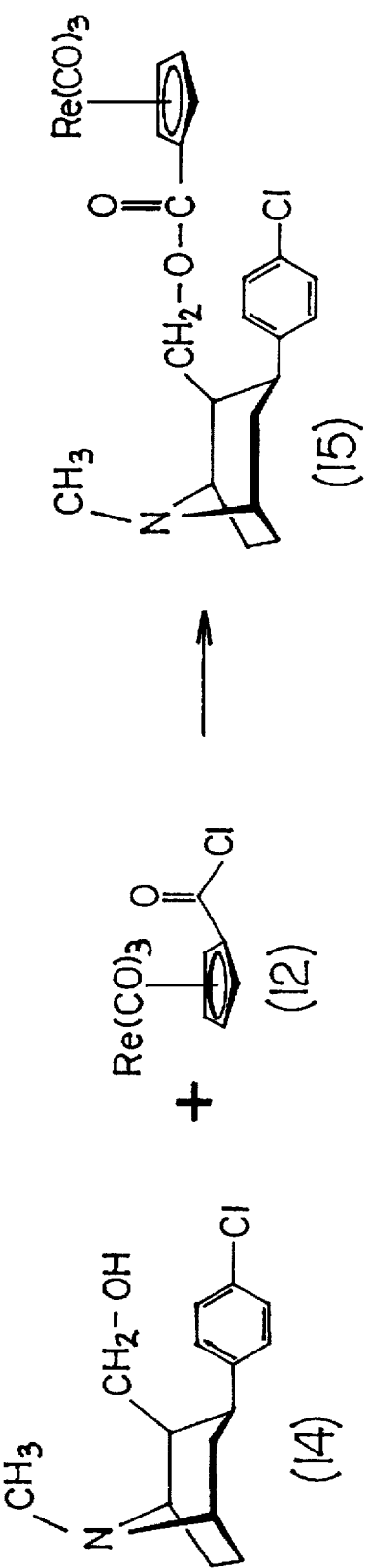
FIG. 5 is another diagram of a series of synthetic steps for preparing another compound of the invention.

As shown in FIG. 5, a solution of N-(2-hydroxypropyl)-2β-hydroxymethyl-3β-(4-chlorophenyl)tropane (14) in toluene (1 g/10 ml) is combined with 1.1 equiv. of triethylamine and 1.1 equiv. of cyclopentadienecarbonylchloride tricarbonylrhenium (12) under nitrogen. After heating at reflux for 30 min., the solvent is removed and the residue passed through a silica gel column equilibrated with hexane/ether/TEA (50/50/5) to give 3β-(4-chlorophenyl)-2β-tricarbonylrheniumcyclopentadienylcarboxymethyl)tropane (15) (RBI-219) in 81% yield. mp=149°–150° C. $^1$H NMR (250 MHz, CDCl$_3$): Δ7.26 (d, J=8.1 Hz, 2H); 7.14 (d, J=8.1 Hz, 2H); 5.82 (m, 1H); 5.66 (m, 1H); 5.33 (m, 2H); 4.48 (dd, J=7.57 Hz, J=11.03 Hz; 1HY); 3.86 (dd; J=10.93 Hz, 1H); 3.26 (m, 1H); 3.20 (m, 1H); 3.07 (m, 1H); 2.22 (s; 3H); 1.61 (m, 3H). Anal. (C$_{24}$H$_{23}$NO$_5$ClRe): CHN.

Procedure for $^{99m}$Tc Radiolabeling

Radiolabeling of ferrocenyl precursors can be carried out using standard procedures known in the art (see Wenzel et al., J. Label. Comp. Radiopharm. 31, 641–650 (1992); Wenzel et al., J. Label. Comp. Radiopharm. 34, 981–987 (1994)).

Figure 6:
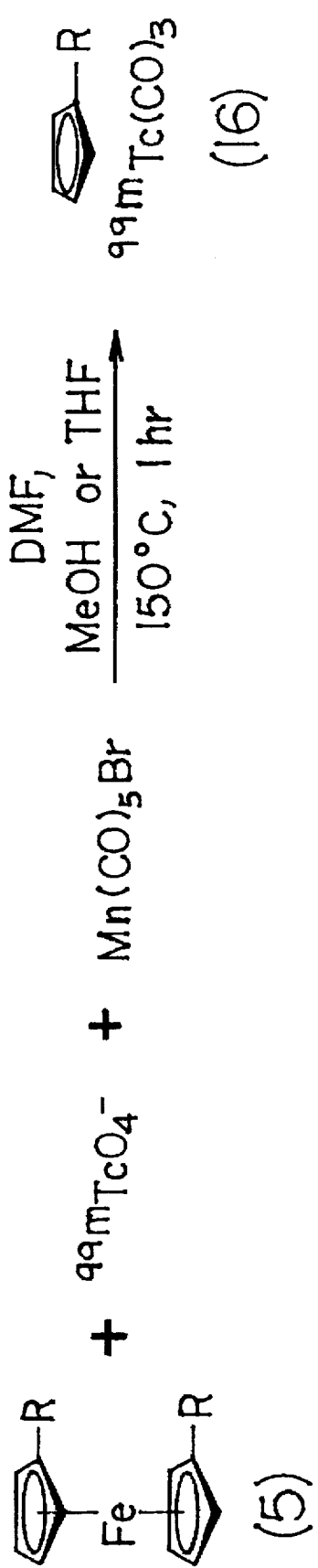
FIG. 6 is a diagram of a series of synthetic steps to produce [$^{99m}$]Tc-labelled compounds of the invention.
Figure 6:
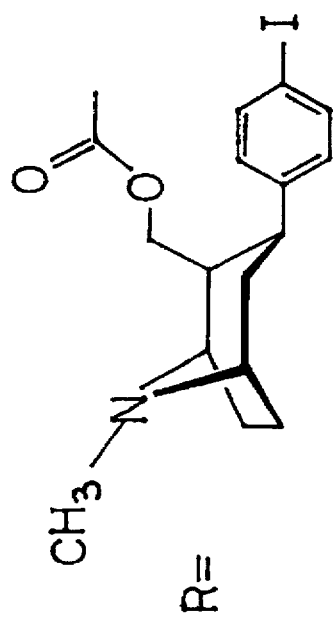

In one embodiment shown in FIG. 6, a ferrocene compound such as 1,1'-bis-[3β-(4-iodophenyl)tropan-2β-ylmethoxycarbonyl] ferrocene from Example 2 above (5) (2 mg) and Mn(CO)$_5$Br are mixed in equimolar ratios in THF, methanol or DMF in a test tube. An equivalent amount of $^{99m}$TcO$_4^-$ eluate (0.5–10 mCi, eluted from a technetium-99m generator) is added. The tube is sealed and heated to 150° C. for 1 h, after which the reaction mixture is purified by semipreparative HPLC (RP-18), and eluted with 0.5 mL H$_2$O and 0.5 mL methanol to isolate the [$^{99m}$Tc]-labelled compound, and to remove insoluble black particles and unwanted $^{99m}$TcO$_2$. Other related ferrocene compounds may also be labelled with $^{99m}$Tc using similar procedures known in the art in combination with the skills of the ordinary skilled practitioner.

Binding Assays for Candidate Compounds

Each of the compounds synthesized above may be tested for binding to various reuptake sites found in homogenates of brain tissue. Each compound is mixed with a crude membrane fraction of homogenates of rat brain corpus striatum (for the dopamine transporter) or frontoparietal cerebral cortex (for the serotonin and norepinephrine transporters). Each compound is tested at six concentrations and in duplicate. Each mixture is incubated in Tris buffer (pH 7.4) containing Na$^+$ (120 nM), following previously reported methods as described in, e.g., Neumeyer et al., J. Med. Chem. 37:1558–1561 (1994); Anderson, J. Neurochem. 48:1887–1896 (1987); Kula et al., Neuropharmacol. 30:89–92 (1992); Habert et al., Eur. J. Pharmacol. 118:107–114 (1985); and Tejani-Butt, J. Pharmacol. Exp. Ther. 260:427–436 (1992). For the dopamine transporter assay, the radioligand was [$^3$H]GBR-12935 (13 Ci/mmol; Kd=1.0 nM) at a test concentration (L)=0.4 nM (for 45 min at 4° C.), with or without 30 μM methylphenidate used to define nonspecific binding (blank). For the serotonin transporter assay, L=0.2 nM [$^3$H]paroxetine (20 Ci/mmol; Kd=0.15 nM [$^3$H]paroxetine (20 Ci/mmol; Kd=0.15 nM (for 60 min at 20° C.); and 1 μM fluoxetine (Lilly Labs., Indianapolis, Ind.) as the blank agent. For the norepinephrine transporter assay, L=0.8 nM [$^3$H]nisoxetine (50 Ci/mmol; Kd=0.8 nM (for 180 min at 4° C.); and 2 μM desipramine (Marion Merrel Dow, Kansas City, Mo.) as the blank agent. All radioligands were from DuPont-NEN, Boston, Mass. Concentration-inhibition curves were computer-fit to determine IC$_{50}$±SEM, and converted to K$_i$ values from the relationship Ki=IC$_{50}$/(1+[L/Kd]).

To evaluate the binding affinities and selectivity of TTCp-tagged phenyltropane analogs for the monoamine transporters, initially, the TRCp or TMCp surrogates were prepared to test their ability to selectively bind to desired transporters in radioreceptor assays using the above-described procedure. The resulting affinities and selectivity of the compounds on transporter sites are comparable to the affinity value of β-CIT used as a reference standard to establish the design of targeted ferrocenyl precursors for $^{99m}$Tc-radiolabeling.

TRCp and TMCp-tagged phenyltropane analogs were evaluated using the above-described radioreceptor binding assay. The results are illustrated in TABLE 1 and compared to results with β-CIT. In TABLE 1, selectivity is defined as the ratio of K$_i$ for the dopamine transporter to the K$_i$ for the serotonin transporter.

TABLE 1

Affinity of β-CIT analogs for the dopamine and serotonin transporter

| Compound | Dopamine Transporter (DA$_T$) (K$_i$, nM) | Serotonin Transporter (5-HT$_T$) (K$_i$, nM) | DA$_T$/5-HT$_T$ Selectivity |
|---|---|---|---|
| RBI-211 | 7.22 ± 1.06 | 34.6 ± 3.4 | 0.21 |
| RBI-219 | 4.41 ± 0.76 | 11.9 ± 1.7 | 0.37 |
| RBI-232 | 2.66 ± 0.33 | 0.56 ± 0.08 | 4.75 |
| RBI-233 | 1.67 ± 0.39 | 0.84 ± 0.06 | 2 |
| RBI-235 | 1.29 ± 0.1 | 0.37 ± 0.04 | 3.49 |
| β-CIT | 1.40 ± 0.2 | 0.46 ± 0.06 | 3.04 |

Although the invention has been shown and described with respect to an illustrative embodiment thereof, it should be appreciated that the foregoing and various other changes, omissions, and additions in the form and detail thereof may be made without departing from the spirit and scope of the invention as delineated in the claims.

What is claimed is:

1. A neuroprobe for mapping monoamine reuptake sites, the neuroprobe having the formula:

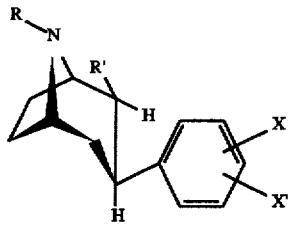

wherein:

X=F, Cl, Br, I, H or alkyl;

X'=F, Cl, Br, I, H or alkyl;

R=alkyl, halogen substituted alkyl, cycloalkyl, halogen substituted cycloalkyl, alkenyl, halogen substituted alkenyl, aryl or halogen substituted aryl; and R'=—(CH$_2$)$_n$Y, wherein Y=—O—C(O)—Z, —C(O)—Z, or —NR"—C(O)—Z; and n=1–6; and wherein further R"=alkyl, cycloalkyl or H; and Z=

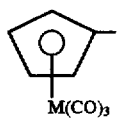

wherein M=rhenium or an isotope of rhenium, manganese or an isotope of manganese, or an isotope of technetium.

2. The neuroprobe of claim 1, wherein X is in the meta or para position.

3. The neuroprobe of claim 1, wherein X' is in the meta or para position.

4. The neuroprobe of claim 1, wherein said isotope of Tc is $^{99m}$Tc.

5. A neuroprobe for mapping monoamine reuptake sites, the neuroprobe having the formula:

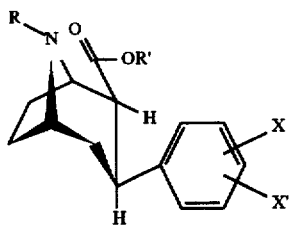

wherein:

X=F, Cl, Br, I, H or alkyl;
X'=F, Cl, Br, I, H or alkyl;
R'=alkyl, halogen substituted alkyl, cycloalkyl, halogen substituted cycloalkyl, alkenyl, halogen substituted alkenyl, aryl or halogen substituted aryl; and
R=—$(CH_2)_n$Y, wherein Y=—O—C(O)—Z, —C(O)—Z, or —NR"—C(O)—Z; and n=1–6; and wherein further R"=alkyl, cycloalkyl or H; and Z=

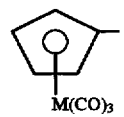

wherein M=rhenium or an isotope of rhenium, manganese or an isotope of manganese, or an isotope of technetium.

6. The neuroprobe of claim 5, wherein X is in the meta or para position.

7. The neuroprobe of claim 5, wherein X' is in the meta or para position.

8. The neuroprobe of claim 5, wherein said isotope of Tc is $^{99m}$Tc.

9. A neuroprobe for mapping monoamine reuptake sites, the neuroprobe having the formula:

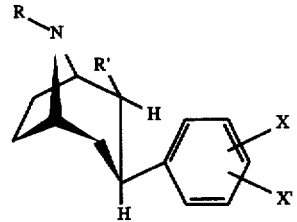

wherein:

X=F, Cl, Br, I, H or alkyl;
X'=F, Cl, Br, I, H or alkyl;
R'=alkyl, halogen substituted alkyl, cycloalkyl, halogen substituted cycloalkyl, alkenyl, halogen substituted alkenyl, aryl or halogen substituted aryl; and
R=—$(CH_2)_n$Y, wherein Y=—O—C(O)—Z, —C(O)—Z, or —NR"—C(O)—Z; and n=14 6; and wherein further R"=alkyl, cycloalkyl or H; and Z=

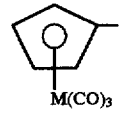

wherein M=rhenium or an isotope of rhenium, manganese or an isotope of manganese, or an isotope of technetium.

10. The neuroprobe or claim 9, wherein X is in the meta or para position.

11. The neuroprobe of claim 9, wherein X' is in the meta or para position.

12. The neuroprobe of claim 9, wherein said isotope of Tc is $^{99m}$Tc.

13. A compound of the formula having the core structure:

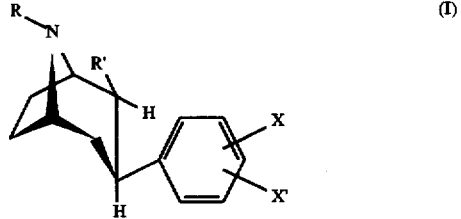

(I)

wherein:

X=F, Cl, Br, I, H or alkyl;
X'=F, Cl, Br, I, H or alkyl;
R=alkyl, halogen substituted alkyl, cycloalkyl, halogen substituted cycloalkyl, alkenyl, halogen substituted alkenyl, aryl or halogen substituted aryl; and
R'=—$(CH_2)_n$Y, wherein Y=—O—C(O)—Z, —C(O)—Z, or —NR"—C(O)—Z; and n=1–6; and wherein further R"=alkyl, cycloalkyl or H; and Z=

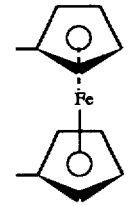

wherein Z is attached to two of said core structure (I), or wherein Z=

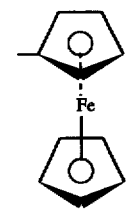

wherein Z is attached to one of said core structure (I).

14. The neuroprobe of claim 13, wherein X is in the meta or para position.

15. The neuroprobe of claim 13, wherein X' is in the meta or para position.

16. The neuroprobe of claim 13, wherein said isotope of Tc is $^{99m}$Tc.

17. A compound of the formula having the core structure:

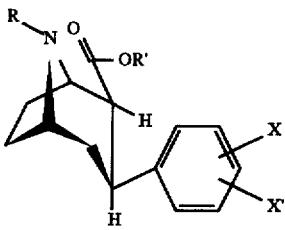
(I)

wherein:
X=F, Cl, Br, I, H or alkyl,
X'=F, Cl, Br, I, H or alkyl;
R'=alkyl, halogen substituted alkyl, cycloalkyl, halogen substituted cycloalkyl, alkenyl, halogen substituted alkenyl, aryl or halogen substituted aryl; and
R=—(CH$_2$)$_n$Y, wherein Y=—O—C(O)—Z, —C(O)—Z, or —NR"—C(O)—Z; and n=1–6; and wherein further R"=alkyl, cycloalkyl or H; and Z=

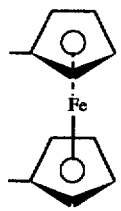

wherein Z is attached to two of said core structure (I), or wherein Z=

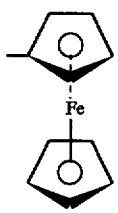

wherein Z is attached to one of said core structure (I).

18. The neuroprobe of claim 17, wherein X is in the meta or para position.

19. The neuroprobe of claim 17, wherein X' is in the meta or para position.

20. The neuroprobe of claim 17, wherein said isotope of Tc is $^{99m}$Tc.

21. A compound of the formula having the core structure:

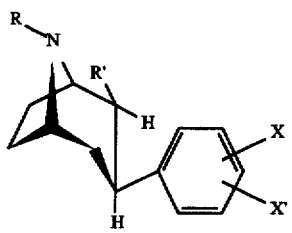
(I)

wherein:
X=F, Cl, Br, I, H or alkyl;
X'=F, Cl, Br, I, H or alkyl;
R'=alkyl, halogen substituted alkyl, cycloalkyl, halogen substituted cycloalkyl, alkenyl, halogen substituted alkenyl, aryl or halogen substituted aryl; and
R=—(CH$_2$)$_n$Y, wherein Y=—O—C(O)—Z, —C(O)—Z, or —NR"—C(O)—Z; and n=1–6; and wherein further R"=alkyl, cycloalkyl or H; and Z=

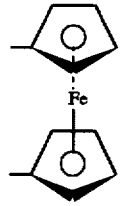

wherein Z is attached to two of said core structure (I), or wherein Z=

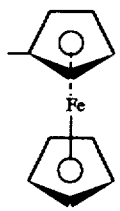

wherein Z is attached to one of said core structure (I).

22. The neuroprobe of claim 21, wherein X is in the meta or para position.

23. The neuroprobe of claim 21, wherein X' is in the meta or para position.

24. The neuroprobe of claim 21, wherein said isotope of Tc is $^{99m}$Tc.

* * * * *

UNITED STATES PATENT AND TRADEMARK OFFICE
CERTIFICATE OF CORRECTION

PATENT NO : 5,700,446
DATED : December 23, 1997
INVENTOR(S): John L. Neumeyer, et al.

It is certified that error appears in the above-identified patent and that said Letters Patent is hereby corrected as shown below:

Column 4, line 45, Under formula, Insert, --(I)--.

Column 4, line 52, "NR'" should read --NR"--.

Column 5, line 23, Under formula, Insert, --(I)--.

Column 7, line 35, "produce" should read --product--.

Column 11, line 5, " 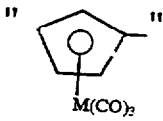 " should read -- 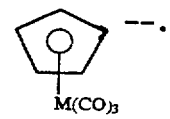 --.

Column 11, line 12, "metal" should read --meta--.

Column 11, line 40, " 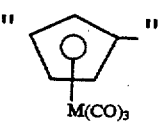 " should read --  --.

Column 12, line 5, "n=14 6" should read --n=1-6--.

UNITED STATES PATENT AND TRADEMARK OFFICE
CERTIFICATE OF CORRECTION

PATENT NO : 5,700,446
DATED : December 23, 1997
INVENTOR(S): John L. Neumeyer, et al.

It is certified that error appears in the above-identified patent and that said Letters Patent is hereby corrected as shown below:

Column 12, line 10, " 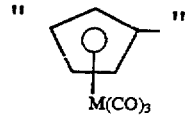 " should read -- 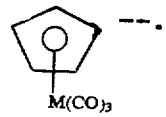 --.

Column 12, line 30, Under formula, Insert, --(I)--.

Column 12, line 64, claim 14, "neuroprobe" should read --compound--.

Column 12, line 66, claim 15, "neuroprobe" should read --compound--.

Column 13, line 1, claim 16, "neuroprobe" should read --compound--.

Column 13, line 12, Under formula, Insert, --(I)--.

Column 13, line 46, claim 18, "neuroprobe" should read --compound--.

Column 13, line 48, claim 19, "neuroprobe" should read --compound--.

UNITED STATES PATENT AND TRADEMARK OFFICE
CERTIFICATE OF CORRECTION

PATENT NO : 5,700,446
DATED : December 23, 1997
INVENTOR(S): John L. Neumeyer, et al.

It is certified that error appears in the above-identified patent and that said Letters Patent is hereby corrected as shown below:

Column 13, line 50, claim 20, "neuroprobe" should read --compound--.

Column 14, line 10, Under formula, Insert, --(I)--.

Column 14, line 44, claim 22, "neuroprobe" should read --compound--.

Column 14, line 47, claim 23, "neuroprobe" should read --compound--.

Column 14, line 49, claim 24, "neuroprobe" should read --compound--.

Signed and Sealed this

Eighteenth Day of April, 2000

Q. TODD DICKINSON

*Attest:*

*Attesting Officer*     *Director of Patents and Trademarks*